United States Patent [19]

Gittos et al.

[11] 3,963,729

[45] June 15, 1976

[54] PHARMACOLOGICALLY ACTIVE PYRIDINE DERIVATIVES

[75] Inventors: Maurice Ward Gittos, Slough; David Anthony Amey, Luton, both of England

[73] Assignee: Aspro-Nicholas Limited, England

[22] Filed: Dec. 18, 1973

[21] Appl. No.: 425,876

[30] Foreign Application Priority Data

Dec. 28, 1972 United Kingdom............... 59761/72

[52] U.S. Cl.................... 260/293.86; 260/247.2 A; 260/247.5 R; 260/268 DK; 260/293.56; 260/326.5 R; 260/465 D; 260/465 E; 260/570.5 P; 260/570.5 C; 424/267
[51] Int. Cl.²........................................ C07D 295/00
[58] Field of Search............... 260/281 GN, 293.86, 260/247.2 A, 293.56, 268 DK

[56] References Cited
FOREIGN PATENTS OR APPLICATIONS
927,330   7/1949   Germany...................... 260/281 GN Primary Examiner—Paul J. Killos
Attorney, Agent, or Firm—Foster York

[57] ABSTRACT

3-Phenyl-3-aminoalkyl-2,6-dioxo-tetra and hexahydropyridines which are substituted in at least one of the 4 and 5 positions of the hydrogenated pyridine ring by a $C_1$–$C_4$ alkyl group or by a divalent radical which together with at least one of the carbon atoms at said 4 and 5 positions forms a carbocyclic ring of 3 to 8 carbon atoms are novel compounds having pharmacological, in particular central nervous system, especially anti-depressant activity. Alkyl esters, dialkylamides and heterocyclic amides of 4-amino-alkyl-4-cyano-4-phenyl-butanoic and but-2-enoic acids substituted in at least one of the 2 and 3 positions by a $C_1$–$C_4$ alkyl group or by a divalent alkylene radical which together with at least one of the carbon atoms at said 2 and 3 positions forms a carbocyclic ring of 3 to 8 carbon atoms are novel intermediates involved in the preparation of the said pharmacologically active compounds. Several methods are disclosed for preparing the pharmacologically active compounds.

3 Claims, No Drawings

PHARMACOLOGICALLY ACTIVE PYRIDINE DERIVATIVES

The present invention relates to compounds having pharmacological, in particular central nervous system, especially anti-depressant, activity and provides pharmacologically active 3-phenyl-3-aminoalkyl-2,6-dioxohydrogenated pyridines and methods for their preparation. The invention provides also pharmaceutical compositions containing one or more of said pyridine derivatives and methods of treatment which comprise administering to an animal a pharmacologically effective dose of one or more of said derivatives.

It is known that 3-phenyl-3-aminoalkyl-2,6-dioxo-tetra- and hexa-hydropyridines optionally substituted in the 1-position by an alkyl group but otherwise unsubstituted in the hydrogenated pyridine ring, i.e. of the formula i:

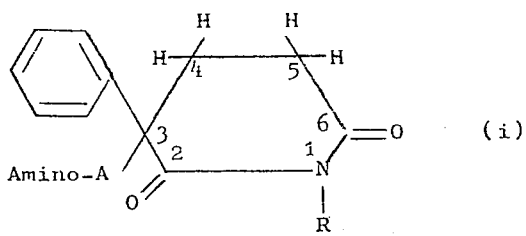

where R represents hydrogen or alkyl and A represents alkylene, have pronounced parasympatholytic activity (see U.S. Patent Specifications Nos. 2,644,424 and 2,749,346). A well known example of such parasympatholytic compounds is Aturbane, i.e. 3-phenyl-3-($\beta$-diethylamino-ethyl)-2,6-dioxo-piperidine (see The Extra Pharmacopoeia, Martindale, 26th Edition at page 304). Although some of these prior art compounds have been found to have central nervous system activity, their pronounced parasympatholytic activity militates against their use in treating depression and other disorders of the central nervous system.

The Inventors have now unexpectedly found that the parasympatholytic activity of 3-phenyl-3-aminoalkyl-2,6-dioxo-tetra- and hexa-hydropyridines can be significantly reduced and a useful central nervous system, especially anti-depressant, activity developed by introducing into the hydrogenated pyridine ring certain substituents in the 4 and/or 5 positions.

According to the present invention, therefore, there are provided 3-phenyl-3-aminoalkyl-2,6-dioxo-tetra and hexa- hydropyridines which are substituted in at least one of the 4 and 5 positions of the hydrogenated pyridine ring by a $C_1$–$C_4$ alkyl group or by a divalent alkylene radical which together with at least one of the carbon atoms at said 4 and 5 positions forms a carbocyclic ring of 3 to 8 carbon atoms, and acid addition salts and quaternary ammonium derivatives thereof. The hydrogenated pyridine ring and the phenyl radical in the 3-position may be substituted further by one or more substituents which are "therapeutically compatible" (as hereinafter defined) with the molecule.

The term "therapeutically compatible" is used in this Specification in relation to a substituent to mean that the presence of that substituent neither destroys the pharmacological activity of the molecule nor so decreases said activity and/or increases the toxicity of the molecule that the therapeutic ratio is reduced to five or below. The therapeutic compatibility of a particular substituent may depend upon the intended site of substitution in the molecule and/or the presence in the molecule of other substituents. Hence a given substituent may be therapeutically compatible in respect of one molecule into which it is introduced but incompatible, i.e. inactivating, in respect of another molecule. The compatibility of any substituent in respect of any compound of the invention can be readily assessed by subjecting the relevant substituted compound to standard screening tests such as those referred to hereinafter. It is well within the ability of the averagely skilled man concerned with the development of new drugs to ascertain which substituents may be present and at what positions in pharmacologically active compounds of the invention.

Examples of substituents likely to be therapeutically compatible with all compounds of the invention are (a) in the phenyl ring, $C_1$–$C_4$ alkyl optionally substituted by hydroxy or $C_1$–$C_4$ alkoxy, hydroxy, $C_1$–$C_4$ alkoxy, halogen and trifluoromethyl and (b) in the hydrogenated pyridine ring, $C_1$–$C_4$ alkyl at the 1, 4 and/or 5 positions and $C_2$–$C_5$ alkoxycarbonyl at the 5 position. It is presently preferred that the phenyl ring should be unsubstituted or substituted by at least one $C_1$–$C_4$ alkoxy, especially methoxy, or halogen, especially chlorine and that the hydrogenated pyridine ring should be substituted in the 4 and/or 5 positions by at least two $C_1$–$C_4$ alkyl, especially methyl.

The alkyl or alkylene radicals (including moieties) in compounds of the present invention may be straight or branched chain, saturated or unsaturated hydrocarbon radicals. Unless otherwise stated, it is preferred that each hydrocarbon radical is saturated and contains 6, more especially 4, carbon atoms or less. Any reference in this Specification to a specific alkyl or alkylene radical having structural isomers includes all of those isomers and mixtures thereof unless a particular isomer is specified. Examples of alkyl radicals are methyl, ethyl, propyl, butyl, amyl, hexyl, ethenyl, ethynyl, propenyl (especially allyl), propynyl (especially propargyl), butenyl and butynyl. Preferred alkyl radicals are methyl and ethyl and preferred alkylene radicals are 1,2-ethylene and 1,3-propylene for the alkylene moiety of the aminoalkyl group and 1,4-butylene and 1,5-hexylene for $R_1$ and $R_2$ or $R_3$.

The amino moiety of the 3-aminoalkyl substituent may be a primary or, preferably, secondary or tertiary amino group. When said amino moiety is secondary or tertiary, the amino nitrogen atom can be attached to, for example, $C_3$ to $C_6$ cycloalkyl or $C_1$ to $C_4$ alkyl optionally substituted by $C_3$–$C_6$ cycloalkyl or by phenyl, which itself may be substituted by, for example, one or more alkoxy groups. Alternatively, when the group is tertiary, the amino nitrogen atom may be part amino group a heterocyclic ring, especially a six-membered alkylene-imino in which one or more carbon atoms optionally are replaced by oxygen or nitrogen. Examples of such alkylene-imino groups are piperidine, piperazine and morpholine. Preferably, the amino group is di($C_1$ to $C_4$) alkylamino, especially dimethyl- or diethyl-amino.

A preferred class of compounds of the present invention are those of formula I:-

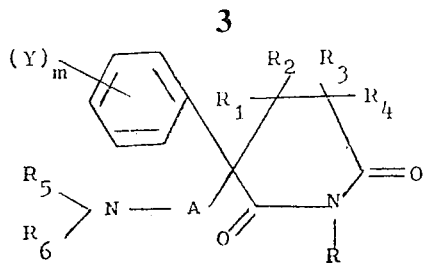

wherein

R represents hydrogen or $C_1$–$C_4$ alkyl;

$R_1$, $R_2$ and $R_3$ independently represent hydrogen or $C_1$–$C_4$ alkyl and $R_4$ represents hydrogen, $C_1$–$C_4$ alkyl or $C_2$–$C_5$ alkoxycarbonyl, provided that at least one of $R_1$, $R_2$, $R_3$ and $R_4$ represents alkyl, or $R_1$ together with $R_2$ or with $R_3$ represents an alkylene radical which together with their immediately adjacent carbon atom(s) of the hydrogenated pyridine ring forms a carbocyclic ring of 3 to 8 carbon atoms and $R_3$ or $R_2$ respectively and $R_4$ are as defined above (not subject to the proviso), or $R_2$ and $R_4$ together represent a second valency bond joining their immediately adjacent carbon atoms, or $R_1$ together with $R_3$ represents a second valency bond joining their immediately adjacent ring carbon atoms and $R_2$ and $R_4$ are as defined above provided that at least one of them represents alkyl;

Y represents $C_1$–$C_4$ alkyl optionally substituted by hydroxy or $C_1$–$C_4$ alkoxy, hydroxy, $C_1$–$C_4$ alkoxy, halogen or trifluoromethyl;

m represents zero or an integer up to 5;

A represents $C_1$–$C_6$ alkylene; and $R_5$ represents $C_1$–$C_4$ alkyl optionally substituted by $C_3$–$C_6$ cycloalkyl, or $C_3$–$C_6$ cycloalkyl and $R_6$ represents hydrogen or $C_1$–$C_4$ alkyl optionally substituted by phenyl, or $R_5$ together with $R_6$ represents an alkylene radical optionally interrupted by oxygen or nitrogen and which together with the amino nitrogen atom constitutes a saturated five or six-membered heterocyclic ring, and acid addition salts and quaternary ammonium derivatives thereof.

An especially preferred class of compounds according to the present invention are those of formula I in which R represents $C_1$–$C_4$ alkyl, especially methyl, or hydrogen;

$R_1$, $R_2$, $R_3$ and $R_4$ independently represent hydrogen or $C_1$–$C_4$ alkyl, especially methyl, provided that at least one of them represents alkyl, or $R_1$ together with $R_3$ represents a second valency bond joining their immediately adjacent ring carbon atoms and $R_2$ and $R_4$ are as defined above provided that at least one of them represents alkyl;

Y represents $C_1$–$C_4$ alkoxy, especially methoxy, halogen, especially chlorine, or trifluoromethyl;

m represents zero or 1;

A represents $C_1$–$C_6$ alkylene, especially of the formula —$(CH_2)_n$— wherein n represents 2, 3 or 4;

$R_5$ represents $C_1$–$C_4$ alkyl, especially methyl or ethyl; and $R_6$ represents hydrogen or, preferably $C_1$–$C_4$ alkyl especially methyl or ethyl, and acid addition salts thereof.

Particularly preferred compounds of the present invention include those of formula Ia:-

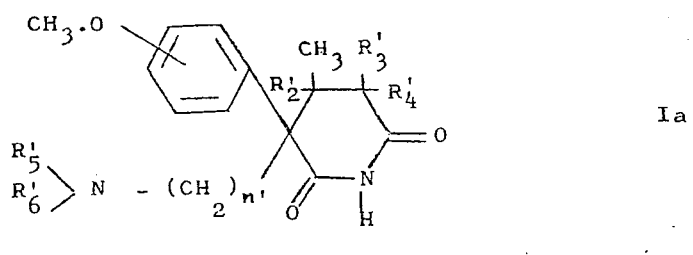

wherein n' represents 2 or 3;

$R_2'$, $R_3'$ and $R_4'$ independently represent hydrogen or methyl, and $R_5'$ and $R_6'$ independently represent methyl or ethyl, and acid addition salts thereof.

The compounds of the present invention which have been pharmacologically screened to date have significantly reduced parasympatholytic activity compared with analogous compounds which are unsubstituted in the 4 and 5 positions and have also a useful level of central nervous system, in particular anti-depressant, activity as measured by standard screening tests. In the majority of compounds of the invention screened to date the presence of an alkyl or alkylene in the 4 and/or 5 position has actually increased the central nervous system activity compared with analogous 4 and 5-unsubstituted compounds.

An indication of the marked effect of introducing a selected substituent into the 4 and/or 5 position of 3-phenyl-3-aminoalkyl-2,6-dioxo-hydrogenated pyridines is given in Tables 1 and 2 following. Table 1 relates to the introduction of one or more methyl groups into the 4 and/or 5 positions of 3-phenyl-3-(β-dimethylamino-ethyl) or (γ-dimethylamino-propyl)-2,6-dioxo-hexa-hydropyridines (i.e. piperidines) and compares the results obtained with Aturbane. Table 2 relates to the introduction of one or more methyl groups into the 4 and/or 5 positions of 3-(methoxy- or chloro-substituted phenyl)-3-(β-dimethylamino-ethyl) or (γ-dimethylamino-propyl)-2,6-dioxopiperidines.

TABLE 1

| m | Y | $R_1$ | $R_2$ | $R_3$ | $R_4$ | $R_5$ | $R_6$ | A | $MYD_{50}$ | POT/PROL. AMPHETAMINE |
|---|---|---|---|---|---|---|---|---|---|---|
| 0 | — | H | H | H | H | $CH_3$ | $CH_3$ | $(CH_2)_2$ | 1.0 | +/o 50 |
| 0 | — | $CH_3$ | H | H | H | $CH_3$ | $CH_3$ | $(CH_2)_2$ | 13 | o/+ 50 |
| 0 | — | $CH_3$ | $CH_3$ | H | H | $CH_3$ | $CH_3$ | $(CH_2)_2$ | 17% at 100 | ++/+++ 50 |
| 0 | — | $CH_3$ | H | $CH_3$ | H | $CH_3$ | $CH_3$ | $(CH_2)_2$ | 2.0 | ++/+++ 50 |
| 0 | — | H | H | $CH_3$ | H | $CH_3$ | $CH_3$ | $(CH_2)_2$ | 1.7 | ++/o 50 |

TABLE 1-continued

| m | Y | $R_1$ | $R_2$ | $R_3$ | $R_4$ | $R_5$ | $R_6$ | A | $MYD_{50}$ | POT/PROL. AMPHETAMINE |
|---|---|---|---|---|---|---|---|---|---|---|
| 0 | — | H | H | H | H | $CH_3$ | $CH_3$ | $(CH_2)_3$ | 0.6 | +/++ 25 |
| 0 | — | $CH_3$ | $CH_3$ | H | H | $CH_3$ | $CH_3$ | $(CH_2)_3$ | 50 | o/+++ 50 |
| 0 | — | H | H | H | H | $C_2H_5$ | $C_2H_5$ | $(CH_2)_2$ | 0.35 | ++/+ 100 |

TABLE 2

| m | Y | $R_1$ | $R_2$ | $R_3$ | $R_4$ | $R_5$ | $R_6$ | A | $MYD_{50}$ | POT/PROL. AMPHETAMINE |
|---|---|---|---|---|---|---|---|---|---|---|
| 1 | 3-$OCH_3$ | H | H | H | H | $CH_3$ | $CH_3$ | $(CH_2)_2$ | 11.0 | o/+++ 50 |
| 1 | 3-$OCH_3$ | $CH_3$ | H | H | H | $CH_3$ | $CH_3$ | $(CH_2)_2$ | 44% at 100 | +/+++ 50 |
| 1 | 3-$OCH_3$ | $CH_3$ | $CH_3$ | H | H | $CH_3$ | $CH_3$ | $(CH_2)_2$ | 25% at 100 | +/+++ 1 to 10 |
| 1 | 3-$OCH_3$ | $CH_3$ | H | $CH_3$ | H | $CH_3$ | $CH_3$ | $(CH_2)_2$ | 25 | +/+++ 1 to 10 |
| 1 | 3-$OCH_3$ | H | H | $CH_3$ | H | $CH_3$ | $CH_3$ | $(CH_2)_2$ | 14.0 | +/+++ 50 |
| 1 | 3-$OCH_3$ | H | H | H | H | $CH_3$ | $CH_3$ | $(CH_2)_3$ | 11.0 | +/++ 25 |
| 1 | 3-$OCH_3$ | $CH_3$ | $CH_3$ | H | H | $CH_3$ | $CH_3$ | $(CH_2)_3$ | 260 | +/+++ 1.0 |
| 1 | 4-Cl | H | H | H | H | $CH_3$ | $CH_3$ | $(CH_2)_3$ | 5.0 | +/+ 25 |
| 1 | 4-Cl | $CH_3$ | $CH_3$ | H | H | $CH_3$ | $CH_3$ | $(CH_2)_3$ | 6% at 100 | +/+++ 50 |

The following abbreviations are used in Tables 1 and 2:

$MYD_{50}$ represents the dose in mg/kg body weight at which 50% mydriasis occurs or, where stated, the percentage mydriases at the specified dose;

POT represents the degree of potentiation of amphetamine stereotypy measured on a scale of 0 to ++;

PROL represents the degree of prolongation of amphetamine stereotypy measured on a scale of 0 to +++.

The mydriatic activity of each of the compounds listed in Tables 1 and 2 was assessed by subcutaneously administering various doses of each compound in a suitable vehicle group of 5 mice and after 30 minutes measuring their pupillary diameters in arbitrary units using a binocular microscope. The mean diameters of each group were then plotted on a dose/response curve taking the mean diameter of a 5 mice group treated with the vehicle as 0 and of a similar group treated with 1mg/kg atropine in the vehicle as 100% mydriasis. The dose of compound required to induce 50% mydriasis was calculated from the dose/response curve. In those cases where the maximum observed effect was less than 50%, the percentage mydriasis at the largest dose tested is shown in the tables. It is generally accepted that the degree of mydriasis is an indication of the extent of parasympatholytic activity; the lower the $MYD_{50}$, the greater the parasympatholytic activity.

The interaction with amphetamine of each of the compounds listed in Tables 1 and 2 was determined using a modification of the method described by Quinton R. M. and Halliwell G. in Nature (Lond.) 1963, 200: 178–9. Various doses of each compound in a suitable vehicle were administered intraperitoneally to groups of 4 rats one hour before similarly administering 5mg/kg of d-amphetamine. The degree of stereotypy of each rat was assessed every 30 minutes following administration of amphetamine for a period of 6 hours using the 6 point scale of Quinton and Halliwell (supra). The mean peak score for each group was compared with that of a control group of 4 rats who received vehicle and amphetamine in the sequence reported above. The control group usually scored 50% of the maximum possible score so the test compound was considered to induce moderate potentiation (+) if the peak score was 60–75% of maximum and marked potentiation (++) if the peak score was 75–100%.

The behaviour of the control group returned to normal before 5 hours post amphetamine. Therefore to indicate the degree of prolongation of amphetamine stereotypy the mean score of each group at 5–6 hours was compared with the peak score. For control groups the value of 5–6 hour score/Peak score × 100 was always less than 30, so a compound was considered to induce slight prolongation (+) if the value between 30 and 55, moderate prolongation (++) if the value was between 55 and 80 and marked prolongation (+++) if the value was between 80 and 100.

In the tables the degree of potentiation is shown first followed by the degree of prolongation and then the lowest dose at which this effect was observed. Thus, for example, +/++mg/kg. 30 indicates that the compound induced moderate potentiation and marked prolongation at 30 mg/kg/

Certain compounds of the invention appear also to have cardiovascular activity.

U.S. Patent Specification No. 2,664,424 teaches that 3-phenyl-3-aminoalkyl-2,6-dioxo-piperidines can be prepared (1) by reacting the corresponding 2-phenyl-2-aminoalkyl-pentane-1,5-diacids or functional derivatives thereof, such as their anhydrides or halides, with ammonia or amines, or (2) by heating the diamides or diammonium salts of said pentane diacids, or (3) by intramolecular acylation of the corresponding pentane-1,5-diacid monoamides or their functional derivatives. In the latter reaction, the monoamide or its functional derivative is not used as a reactant but is formed during the course of the treatment of the corresponding pentane-1,5-diacid-dinitriles, nitrile esters or, more usually, mononitriles with condensing agents to yield the desired dioxopiperidines. Analogous methods of preparing 3-phenyl-3-aminoalkyl-2,6-dioxotetrahydropyridines from 2-phenyl-2-aminoalkyl-pent-3-ene-1,5-diacids and derivatives thereof are described in U.S. Pat. Specification No. 2,749,346.

All of the aforementioned prior art processes can be used to prepare compounds of the present invention from the corresponding 2-phenyl-2-aminoalkyl-3 and-/or 4-substituted-pentane or pent-3-ene-1,5-diacids and derivatives thereof. However, unlike the 3 and 4 unsubstituted pentane and pentene reactants described in the prior art supra, the 3 and/or 4 substituted pentane and pentene reactants required to prepare the present compounds cannot be obtained via Michael additions of the corresponding aminoalkyl benzyl cyanides across the unsaturated bond of acrylic or propiolic esters. Alternative methods of preparing the required reactants had therefore to be invented and these methods are described hereinafter. Further, a method of preparing certain of the compounds of the present invention directly from intermediates first used to obtain the said diacid reactants was also invented and is described hereinafter.

Accordingly, the present invention provides a method of preparing the compounds of the invention, which method comprises treating with ammonia or an amine in manner known per se a corresponding 2-phenyl-2-aminoalkyl-pentane 1,5-diacid or 2-phenyl-2-aminoalkyl pent-3-ene-1,5-diacid, or a functional derivative of either of those acids. Alternatively, the desired compounds of the present invention can be prepared by heating a diamide or diammonium salt of either of the aforementioned diacids.

The present invention further provides another alternative method of preparing the compounds of the invention which comprises treating with a condensing agent in manner known per se a mononitrile, dinitrile or nitrile ester of a corresponding 2-phenyl-2-aminoalkyl-pentane-1,5-diacid or 2-phenyl-2-aminoalkyl-pent-3-ene-1,5-diacid. It is preferred that the said nitrile reactant is a nitrile ester. The oxygen atom of the alkoxy moiety of the ester group of the nitrile esters may be replaced by another element of Group VIa of Mendeleef's Periodic Classification, especially sulphur. Unless otherwise specified or implied the references hereinafter to ester groups are to be understood to include said Group VIa analogues.

According to one embodiment of the present invention, therefore, there is provided a method of preparing compounds of the invention, which method comprises treating in manner known per se the corresponding alkyl ester of 4-aminoalkyl-4-cyano-4-phenyl-3 and/or 2-alkyl or alkylene-butanoic or but-2-enoic acid (i.e. a pentane or pent-3-ene 1,5-diacid nitrile ester) with a condensing agent. In terms of preparing compounds of formula I, the ester reactant will be of formula 2:

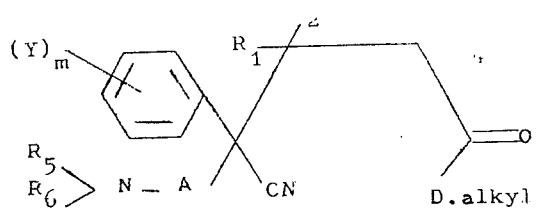

wherein D represents a Group VIa element especially sulphur or, more usually, oxygen, and the other symbols are as defined in connection with formula I. It will be noted that compounds of the invention in which the 1 position of the hydrogenated pyridine ring is substituted cannot be prepared directly by this method.

The condensing agent can be a Bronsted or Lewis acid such as those disclosed in U.S. Patent Specification No. 2,664,424, viz. concentrated sulphuric acid, acetic anhydride, tin tetrachloride, titanium tetrachloride, boron trifluoride etherates, zinc chloride, aluminium chloride or mixtures thereof. It is preferred that the condensing agent is a mixture of a strong protonating agent, for example, sulphuric or perchloric acid, and a nucleophile, for example acetic acid or anhydride or propionic acid. Usually, the protonating acid will constitute 25 to 50% by volume of the mixture and the reaction will be carried out at an elevated temperature, advantageously in the range of 60° to 120°C, for a period of 1 to 30 hours. The resultant mixture is then neutralised with a weak base, for example ammonium hydroxide, to a pH in the range of 7.5 to 9.5. Said neutralisation is strongly exothermic and accordingly is advantageously carried out with cooling to a temperature in the range of 0° to 30°C. The desired hydrogenated pyridine derivative can be isolated by filtration or by extraction into a suitable solvent, for example chloroform or ether, and subsequent recovery from the solvent.

The nitrile esters in which the 5-position of the hydrogenated pyridine ring carries at least one hydrogen atom can be prepared from a corresponding 4-aminoalkyl-4-cyano-4-phenyl-1-alkoxy or Group VIa element analogue-1-dialkylamino or saturated heterocyclic amino-but-1-ene or but-1,2-diene. In terms of preparing compounds of formula I, the said butene or butadiene starting material will be of the formula 3:

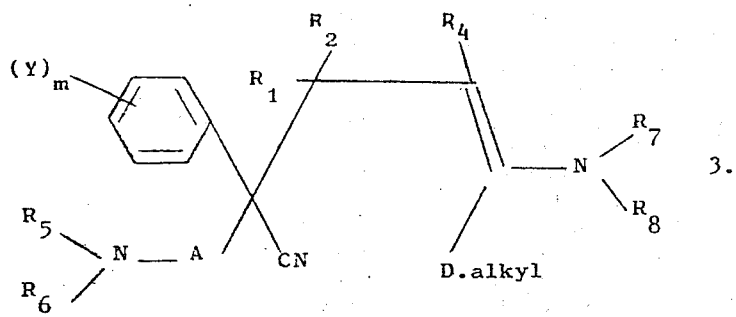

wherein

D represents a Group VIa element, especially oxygen or sulphur;

$R_7$ and $R_8$ represent the same or different alkyl groups or together represent a saturated alkylene radical optionally substituted by oxygen or nitrogen, which alkylene radical with the adjacent nitrogen atom forms a heterocyclic ring; and the remaining symbols are as defined in connection with formula I.

The process for converting the butene or butadiene starting materials into the desired nitrile ester comprises a first step in which the corresponding 4-aminoalkyl-4-phenyl-3 and/or 2 alkyl or alkylene-1-dialkoxy-1-alkoxy or Group VIa element analogue-butene or but-2-ene is formed by treating the starting material with, for example, a strong non-nucleophilic acid, such as methane sulphonic acid, in the presence of a mixture of a $C_1$–$C_6$ primary alcohol, such as ethanol, and an orthoester, such as ethyl orthoformate. The reaction usually will be carried out at an elevated temperature, advantageously in the range 60° to 120°C and preferably under reflux conditions. When the intermediate compound is required for the preparation of a compound of formula I, it will have the formula 4:

acid) and the resultant solution held at 100°C for at least 1 hour before pouring onto an ice and ammonium hydroxide mixture. The amount of ammonium hydroxide in the mixture should be in excess of that required to exactly neutralise the acid and sufficient to bring the pH of the final solution into the range of 7.5 to 9.5. The desired compound of the invention is then extracted

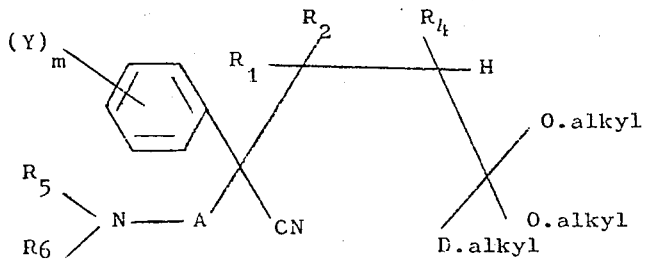

wherein the symbols are as defined in connection with formulae 1 and 3.

The butane or butene intermediate prepared as above is then hydrolysed, usually in situ, by treatment with, for example, water at an elevated temperature, especially 60° to 90°C, to the desired nitrile ester. This ester may then be treated with a condensing agent to form a compound of the invention in the manner described above. However, since the ester is liable to a competitive reaction with the original amine starting material, it is preferred to subject the reaction product of the hydrolysis step to a Schotten-Baumann reaction with, for example, p-toluene sulphonyl chloride.

In a typical process for preparing compounds of the invention from the aforementioned butene or butadiene starting materials, the starting material (1 equivalent) is dissolved in ethanol and ethyl orthoformate (5 equivalents) and methane sulphonic acid (3 equivalents) added to the resultant solution. Said solution is refluxed overnight and then poured into water. The aqueous mixture is maintained at 70°C for 30 minutes and then cooled, washed with ether, adjusted to pH7 and added to a suspension of p-toluene sulphonyl into a suitable solvent such as chloroform and subsequently recrystallised from a suitable solvent, e.g. ethanol.

The nitrile amide contaminant referred to above is also converted into the desired compound of the invention under the aforementioned conditions if the heating period is sufficiently long. The nitrile amide can be obtained in a relatively pure state by treating a 4-aminoalkyl-4-cyano-4-phenyl-3 and/or 2 alkyl or alkylene-1alkoxy or Group VIa element analogue 1-dialkylamino or saturated heterocyclic amino-but-1-ene or but-1,2-diene with sodium iodide and a strong acid, e.g. methane sulphonic acid, in a solvent, e.g. ethanol. It is preferred to heat the reaction mixture. Any iodine produced during the reaction can be destroyed by treatment with, for example, sodium bisulphite solution. The resultant amide can then be converted into a compound of the invention by treatment with a condensing agent using substantially the same reaction conditions as those described above with reference to the treatment of nitrile esters. When the aforementioned nitrile amide is required for the preparation of compounds of formula I, it will have the formula 3a:

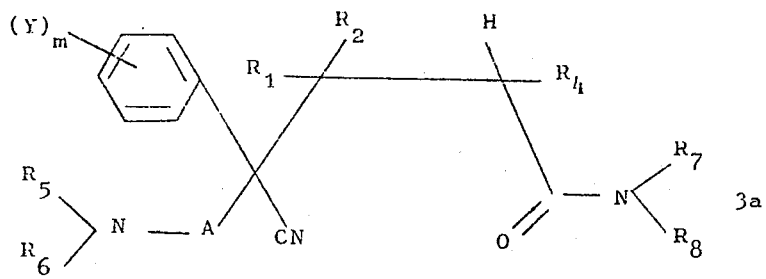

chloride in 5N sodium hydroxide. The mixture is shaken vigorously for 15 minutes with cooling, if necessary. The product is extracted into ether, the ethereal solution washed with dilute hydrochloric acid and the aqueous solution added to saturated potassium carbonate solution. The basic organic materials are then extracted into ether and recovered by drying over magnesium sulphate and evaporating off the solvent. The nitrile ester product thus obtained will be contaminated with some corresponding nitrile amide which may be separated by column chromatography. This nitrile ester, after separation or still in admixture with the contaminant amide, is dissolved in acetic acid (1ml per gm of ester) and sulphuric acid (equal volume with acetic wherein the symbols are as defined in connection with formula 3.

It has been found that the butene and butadiene starting materials referred to above can readily be converted directly into the desired compounds of the invention by treatment with a condensing agent. Accordingly, a preferred embodiment of the present invention provides a method of preparing compounds of the invention, which method comprises reaction of the corresponding 4-aminoalkyl-4-cyano-4-phenyl-3 and/or 2-alkyl or alkylene-1-alkoxy or Group VIa element analogue-1-dialkylamino or saturated heterocyclic amino-but-1-ene or but-1,2-diene with a condensing agent. Suitable agents and reactions conditions are as set forth above in connection with conversion of nitrile esters into compounds of the invention. In a typical process the butene or butadiene reactant (1 gm) is dissolved in acetic acid (1.5 ml) and sulphuric acid (1 ml) and the resultant solution maintained at a temperature of 100°C for 24 hours. The solution is allowed to cool and then is poured onto a mixture of ice and sufficient ammonium hydroxide to neutralise the acids and bring the pH of the final solution into the range 7.5 to 9.5. The desired product is then isolated by extraction into chloroform and subsequently recrystallised from a suitable solvent, e.g. ethanol. The compounds of the invention prepared directly by preferred process above have at least one hydrogen atom in the 5-position of the hydrogenated pyridine ring. An alkyl group can be introduced into the molecule in place of said hydrogen atom by first alkylating the butene or butadiene starting material to form a diquaternary ammonium derivative thereof and then treating that derivative with the condensing agent and, if required, dequaternising the product thus obtained. The alkylation and dequaternisation may be carried out in manner known per se. Preferably, the alkylation is performed by treating the starting material with a compound including an incipient alkyl carbonium ion ($R_4^+$ in the case of preparing compounds of formula I) usually in a polar aprotic solvent such as dichlormethane.

Alkyl carbonium ions are positively charged intermediates formed by the removal of a pair of electrons from a carbon atom of a monovalent aliphatic hydrocarbon radical. They have only a transient existence as such but do exist in solvated form such as in trialkyloxonium (e.g. $(R_4)_3O^+$) and dialkyloxycarbonium (e.g. $HC^+(OR_4)_2$) ions. Conveniently such solvated ions are supplied to the reaction mixture in combination with such non-nucleophilic anions as $BF_4^-$. Another suitable source of incipient alkyl carbonium ions are the alkyl esters of very strong acids such as fluorosulphonic acid ($FSO_3H$) and perfluorinated alkyl sulphonic acids. In the present case suitable compounds including an incipient carbonium ion are $C_1$–$C_4$ alkyl esters of fluorosulphonic acid and di-$C_1$–$C_4$-alkyl-sulphates.

But-1-ene and but-1,2-diene starting materials for the processes referred to above can be prepared by treating the corresponding alkali metal, preferably sodium, α-(aminoalkyl)-benzylcyanide with the corresponding 3 and/or 2-alkyl or alkylene-1-alkoxy or Group VIa element analogue-prop-2-enylidine or prop-2-ynylidine iminium salt in a polar aprotic solvent such as dimethylsulphoxide or 1,4-dioxan. In terms of preparing the compounds of formula 3, the said reactants will be of the formula 5 and 6 respectively:

with formulae 1 and 3.

Usually, a solution of the iminium salt will be added dropwise to a solution of the benzylcyanide whilst, if necessary, cooling the reaction mixture to dissipate the heat of reaction and then the reaction mixture maintained at a temperature of up to about 75°C for a period of up to about 3 hours. In a typical process, the iminium salt in dimethylsulphoxide is added dropwise with stirring to an equivalent amount of the benzyl cyanide in the same solvent. When the addition is complete, the mixture is maintained at 60°C for 2 hours, allowed to cool and transferred to a suitable vessel where the solvent is removed under pressure. The residue is triturated with ether and the mixture filtered. The filtrate is then evaporated down to a residue of the desired butene or butadiene starting material, which residue may be used in the aforementioned processes without further treatment. In a typical process a solution of triethyloxonium tetrafluoroborate (1 equivalent) in dichloromethane is added to an acryloyl or propioloyl amide (1 equivalent) in the same solvent. The mixture is refluxed for 30 minutes and then the solvent removed under reduced pressure. The product is dissolved in dimethylsulphoxide for immediate use or is triturated with ethylacetate and the solid filtered off and dried.

The alkali metal benzyl cyanides can be prepared in situ by treating the corresponding benzyl cyanide with a very strong alkali metal base such as dimsyl sodium (obtained by dissolving sodium hydride in dimethylsulphoxide) in a polar aprotic solvent. The temperature of the reaction may be up to about 50°C but should be below the boiling point of the solvent.

The iminium salts are believed to be new compounds and can be prepared by treating the corresponding alkyl or alkylene substituted acryloyl or propioloyl amide or its Group VIa element analogue with an alkylating agent, preferably a compound including an incipient carbonium ion in a polar solvent. usually equimolar amounts are used at a temperature in the range 20° to 80°C, preferably under reflux conditions.

The substituted acryloylamides and their Group VIa analogues can be prepared by treatment in an inert organic solvent of the corresponding acryloyl anhydride, chloride or bromide or analogue thereof with the corresponding dialkylamine or saturated heterocyclic amine at a temperature in the range −10° to +15°C. In a typical process, an acryloyl chloride (1 equivalent) is dissolved in dry ether or benzene and then ice-cooled. The amine (2 equivalents) is added to the solution whilst stirring well and when the addition is complete the mixture is warmed for a few minutes, cooled and

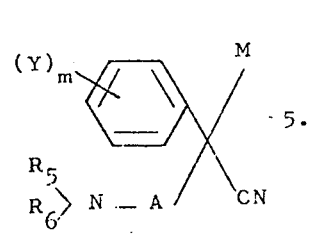

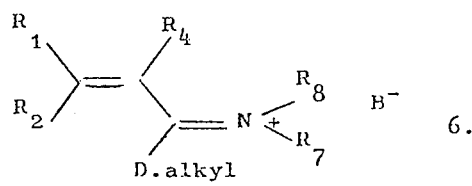

wherein
M represents alkali metal;
$B^-$ represents a non-nucleonphilic anion;
and the other symbols are as defined in connection amine hydrochloride filtered off and the solvent removed. The amide product thus obtained if solid may be recrystallised from petrol or if liquid may be distilled.

The substituted propioloyl amides and their Group VIa analogues can be prepared from alkali metal salts of the corresponding terminal acetylene by reaction with a carbamoyl chloride or bromide. Usually, the reaction will be carried out at a temperature in the range −20° to +40°C in a polar aprotic solvent under an inert gas atmosphere. The alkali metal salt reactant can be obtained by treating a terminal acetylene with a strong alkali metal base in an aprotic solvent at a temperature in the range −50° to −20°C under an inert gas atmosphere. In a typical process, a terminal acetylene in approximately 50% excess is bubbled through a solution of butyl lithium in hexane at −40°C and under a nitrogen atmosphere. The mixture is stirred and allowed to warm up to about −20°C, whence dry tetrahydrofuran is added to dissolve the lithium salt of the acetylene and then a solution of carbamoyl chloride also in dry tetrahydrofuran is added. The mixture is allowed to increase to room temperature and is then heated to 50°C for 15 minutes. Lithium chloride is filtered off and the propioloyl amide isolated by removal of the solvent. In exceptional cases, it may be necessary to dissolve the lithium chloride in a minimum of water and then extract the amide into chloroform.

The alkyl esters of 4-aminoalkyl-4-cyano-4-phenyl-3- and/or 2-alkyl or alkylene-but-2-enoic acids used for producing compounds of the invention may be prepared by treating an alkali metal, preferably sodium, α-aminoalkyl-benzyl-cyanide with an alkyl ester of 3 and/or 2-alkyl or alkylene-prop-1-enoic acid having a leaving group in the 3-position. By a leaving group we mean a group which under the reaction conditions employed will preferentially form an alkali metal salt. Suitable leaving groups include p-toluene sulphonyl or benzene-sulphonyl. Usually, the reaction will be carried out in a polar aprotic solvent such a dimethylsulphoxide and preferably at a temperature in the range 50° to 100°C.

In terms of preparing the compounds of formula 2 wherein $R_1$ and $R_3$ together represent a second valency bond between the adjacent carbon atoms, the said propenoic acid alkyl esters are of the formula 7;

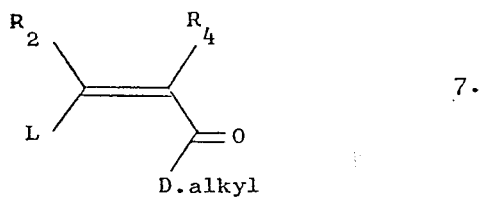

wherein L represents the leaving group and the other symbols are as defined in connection with formulae 1 and 2. When $R_2$ is alkyl with an α-hydrogen atom, the reaction product is an isomer of the said compound of formula 2 in which the 2,3 bond is unsaturated and an ethylene double bond extends from the 3-position to the residue of the group $R_2$ after removal of the α-hydrogen atom i.e. of the formula

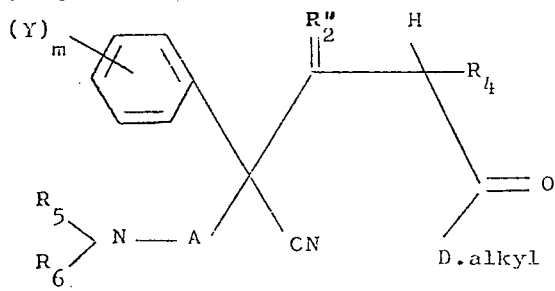

wherein $R_2''$ represents the residue of an alkyl group of 1 to 4 carbon atoms having an α-hydrogen atom after removal of that atom, and the remaining symbols are as defined in connection with formula 2. This isomer may be converted into a compound of the invention in exactly the same manner as the compounds of formula 2.

The alkyl esters of 4-aminoalkyl-4-cyano-4-phenyl-3-alkyl or alkylene-2-alkoxycarbonyl-butane-1-carboxylic acids may be prepared by treating an alkali metal, preferably sodium, α-aminoalkylbenzyl cyanide with a dialkyl ester of 2-alkyl or alkylene-ethylene-1,1-dicarboxylic acid. In terms of preparing compounds of formula 1, the said diesters are of the formula 8:

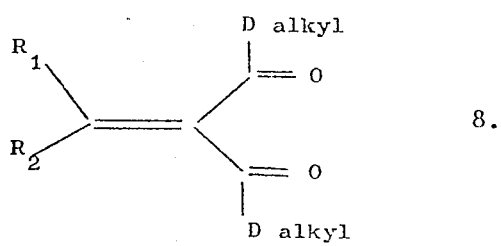

wherein the symbols are as defined in connection with formulae 1 and 2. It is doubtful, however, if the process would proceed as desired when both $R_1$ and $R_2$ represent alkyl groups having α-hydrogen atoms.

Usually the aforementioned reaction will take place by heating the reactants in an anhydrous polar solvent such as dimethyl sulphoxide or dioxan to a temperature in the range of 40° to 100°C, preferably at 50° to 70°C, for a period of up to about 3 hours. The reaction mixture is then cooled and neutralised with a weak anhydrous acid such as acetic acid. After removal of the solvent, the residue may be dissolved in water, added to saturated potassium carbonate solution and the desired nitrile ester extracted into ether.

In all of the alkyl ester reactants referred to above, it is preferred that the Group VIa element is sulphur or, especially, oxygen and that the alkyl group should contain from 1 to 6, more especially 1 to 4 carbon atoms. Preferred alkyl groups are methyl and ethyl. Further, the 1-amino group of reactants containing an amino group other than in the amino-alkyl group desired for the product compound of the invention is preferably a di($C_1$–$C_4$) alkyl amino or saturated six membered heterocyclic amino optionally including oxygen and further nitrogen ring atoms such as piperidine, piperazine and, especially, morpholine.

One or other of the processes described above can be employed to prepare all of the compounds of the present invention although in some cases direct formation of a particular compound may not be possible. However, it will be readily apparent to those skilled in the art that those compounds which cannot be prepared directly by the said processes can be obtained by methods known per se from related compounds of the invention which can be prepared directly. In other cases, it may be desirable for a substituent in a compound prepared according to one of the aforementioned processes to be converted into another substituent to provide another compound of the invention. These conversions are carried out in manner known per se. Thus, for example, a compound of formula 1 in which $R_4$ represents alkoxycarbonyl can readily be converted into the corresponding compound in which $R_4$ represents hydrogen by heating with a mineral acid, for example hydrochloric acid in acetic acid solution. Further, the tetrahydropyridine compounds of the invention can readily be reduced in manner known per se to the corresponding piperidines of the invention.

The compounds produced by the foregoing process may be isolated either per se or as acid addition salts or quaternary ammonium derivatives thereof.

The acid addition salts are preferably the pharmaceutically acceptable, non-toxic addition salts with suitable acids, such as those with inorganic acids, for example hydrochloric, hydrobromic, sulphuric or phosphoric acids, or with organic acids, such as organic carboxylic acids, for example, glycollic, maleic, hydroxymaleic, malic, tartaric, citric, salicylic, o-acetyloxybenzoic, nicotinic or isonicotinic acid, or organic sulphonic acids for example methane sulphonic, ethane sulphonic, 2-hydroxyethane sulphonic, toluene-p-sulphonic or napthalene-2-sulphonic acid. Apart from pharmaceutically acceptable acid addition salts, other salts are also included within the scope of acid addition salts such as, for example, those with picric or oxalic acid; they may serve as intermediates in the purification of the compounds or in the preparation of other, for example, pharmaceutically acceptable, acid additon salts, or are useful for identification, characterisation or purification of the bases.

A resulting acid addition salt may be converted into the free compound according to known methods, for example, by treating it with a base, such as with a metal hydroxide or alkoxide, for example an alkali metal or alkaline earth metal hydroxide, for example, lithium hydroxide, sodium hydroxide, potassium hydroxide or calcium hydroxide; with a metal carbonate, such as an alkali metal or an alkaline earth metal carbonate or hydrogen carbonate, for example, sodium, potassium or calcium carbonate or hydrogen carbonate; with ammonia; or with a hydroxyl ion exchange preparation, or with any other suitable reagent.

A resulting acid addition salt may also be converted into another acid addition salt according to known methods; for example, a salt with an inorganic acid may be treated with a metal salt, for example a sodium, barium or silver salt, of an acid in a suitable diluent, in which a resulting inorganic salt is insoluble and is thus removed from the reaction medium. An acid addition salt may also be converted into another acid addition salt by treatment with an anion exchange preparation.

Quaternary ammonium derivatives of the compounds of this invention are particularly those formed by reaction with lower alkyl halides, for example, methyl, ethyl, or propyl chloride, bromide or iodide; di-lower alkyl sulphates, for example, dimethyl or diethyl sulphate; lower alkyl lower alkane sulphonates, for example, methyl or ethyl methane sulphonate or ethane sulphonate; lower alkyl aryl sulphonates, for example methyl or ethyl p-toluene sulphonates; and phenyl-lower alkyl halides, for example benzyl or phenethyl chloride, bromide or iodide. Also included are the quaternary ammonium hydroxides and the quaternary ammonium compounds having as anions those of other inorganic or organic acids, for example those of the acids used for the preparation of the previously-mentioned acid addition salts. The quaternary ammonium compounds do not have the desired pharmacological activity but are useful for separation and identification purposes.

In the composition aspect of the invention, there are provided pharmaceutical formulations in which form the active compounds of the invention will normally be utilised. Such formulations are prepared in a manner known per se in the pharmaceutical art and usually comprise at least one active compound of the invention in admixture or otherwise in association with a pharmaceutically acceptable carrier thereof. For making these formulations, the active ingredient will usually be mixed with a carrier, or diluted by a carrier, or enclosed or encapsulated in a capsule, sachet, cachet, paper or other container. A carrier or diluent may be a solid, semi-solid or liquid material which serves as a vehicle, excipient, or medium for the active ingredient. Some examples of such diluents or carriers are lactose, dextrose, sucrose, sorbitol, mannitol, starches, gum acacia, calcium phosphate, liquid paraffin, cocoa butter, oil of theobroma, alginates, tragacanth, gelatin, syrup B.P., methyl cellulose, polyoxyethylene benzoate, talc, magnesium stearate or mineral oil.

The formulations of the invention may be adapted for enteral or parenteral use and may be administered to a subject requiring treatment in the form of tablets, capsules, suppositories, solutions, suspensions or the like. The dosage required for the treatment of any animal willl depend upon the route of administration and will usually fall within the range 0.01 to 250 mg/kg daily. In the case of humans much further work remains to be done before a safe and effective dosage can be recommended but it is expected that said dosage will be within the range 0.1 to 100 mg/kg daily. Accordingly, formulations of the invention are likely to be provided in dosage unit forms containing from 1 to 1000 mg, more likely 5 to 500 mg and most likely 10 to 250 mg.

The following Examples will further illustrate the preparation of the novel compounds of this invention. All temperatures are given in degrees Centigrade.

EXAMPLE 1

Preparation of 3-(m-methoxyphenyl)-3-($\gamma$-N,N-dimethylaminopropyl)-4,4-dimethyl-2,6-dioxo-piperidine Sodium hydride (3.36 g of a 50% suspension in oil, 0.07 mole) is placed in a 3-necked round-bottomed flask and the mineral oil removed by washing (twice) with 40–60 petrol. The flask is then fitted with a stirrer, condenser and nitrogen bleed and dry dimethylsulphoxide (75 ml) added. The mixture is stirred in a nitrogen atmosphere at temperatures of up to 80° until the sodium hydride has completely dissolved and evolution of hydrogen has ceased. The resultant solution of dimsyl sodium is then cooled and $\alpha$(3-N,N-dimethylaminopropyl)-m-methoxy benzyl cyanide (16.2 gm 0.07 mole) added followed by dropwise addition of a solution in dry dimethylsulphoxide of 3,3-dimethyl-1-ethoxy-prop-2-enylidine morpholinium tetrafluoroborate (20 gm, 0.07 mole). When addition is complete, the mixture is held at 50° for 30 minutes, cooled, transferred to a single-necked round-bottomed flask and the solvent removed under reduced pressure (1 mm Hg). The residue is triturated with dry ether and sodium tetrafluoroborate filtered off. The solid is further washed with dry ether and the washings added to the filtrate. The ether is then evaporated off to leave 4-(m-methoxyphenyl)-4-($\gamma$-N,N-dimethylaminopropyl)-4-cyano-3,3-dimethyl-1-ethoxy-1-morpholino-but-1-ene (28.5 gm, 95%).

The but-1-ene product above is dissolved in acetic acid (45 ml) and sulphuric acid (30 ml) added. The resultant mixture is maintained at 100° until cyclisation is complete, as determined by working-up an aliquot and studying the infra-red spectrum of the product. The solution is cooled and poured into excess ammonia/ice, the pH adjusted to about 8 with aqueous ammonia and the solution extracted with chloroform (three times). The organic solutions are combined, dried, filtered and the solvent removed. The residual dione is crystallised and recrystallised from ethanol to give white crystals of 3-(m-methoxyphenyl)-3-($\gamma$-N,N-dimethylaminopropyl)-4,4-dimethyl-2,6-dioxo-piperidine, m.pt. 167°–9°.

The 3,3-dimethyl-1-ethoxy-prop-2-enylidine morpholinium tetra-fluoroborate reactant was obtained as follows:

Morpholine (2 equivalents) is added to a well-stirred ice-cooled solution in dry ether of 3,3-dimethylacryloyl chloride (1 equivalent) and when addition is complete, the mixture is warmed for a few minutes. The mixture is then cooled, filtered, the solvent removed and the residue recrystallised from 60–80 petrol to 3,3-dimethylacryloyl morpholine m.pt. 52°–4°.

The 3,3-dimethylacryloyl morpholine (1 equivalent) obtained as above was dissolved in dichloromethane and triethyl oxonium tetrafluoroborate (1 equivalent) in dichloromethane added to the resultant solution. The mixture was refluxed for 30 minutes, the solvent removed under reduced pressure, and the residue triturated with ethyl acetate and the solid filtered off and dried to yield the desired iminium tetrafluoroborate.

EXAMPLE 2

Preparation of
3-(m-methoxyphenyl)-3-($\beta$-N,N-dimethylaminoethyl)-4-ethyl-5-ethoxycarbonyl-2,6-dioxo-tetrahydropyridine Sodium hydride (2.83 g of a 50% suspension in oil) is dissolved in dry dimethylsulphoxide and $\alpha$-(2-N,N-dimethylaminoethyl)-m-methoxy benzyl cyanide (12.9 g) added. Diethyl-1-(benzenesulphonyloxy)-propylidine malonate (21 g) is added slowly to the resultant mixture. The solvent is then removed and the residue "topped" at 0.1 mm Hg and 150° to leave crude ethyl-4-cyano-4-($\beta$-N,N-dimethylaminoethyl)-4 (m-methoxyphenyl)-3-ethyl-2-ethoxycarbonyl-but-2-enoic acid.

A solution of said crude ester (6.3 gm) in acetic acid (10 ml) and sulphuric acid (12 ml) was held at 100° for 1 hour and then cooled. The cooled mixture was poured onto ammonia/ice, the pH adjusted to 8 by addition of aqueous ammonia and the precipitated gum triturated with methanol. The solid was filtered off and recrystallised from aqueous methanol to give white crystals of 3(m-methoxyphenyl)-3-($\beta$N,N-dimethylaminoethyl)-4-ethyl-5-ethoxycarbonyl-2,6-dioxo-tetrahydropyridine, m.pt. 160°–2°.

EXAMPLE 3

Preparation of
3(m-methoxyphenyl)-3-($\gamma$-N,N-dimethylamino propyl)-4,4-dimethyl-2,6-dioxo-piperidine $\alpha$-(3-N,N-Dimethylaminopropyl)-m-methoxy benzyl cyanide (23.2 g, 0.1 mole) is added to a solution (150 ml) of dimsyl sodium prepared as described in Example 1. A solution of 3,3-dimethyl-1-ethoxy-prop-2-enylidene morpholinium fluorosulphonate (0.1 mole, prepared from 16.9 g of the free base) in dimethylsulphoxide (50 ml) is then added dropwise. When the addition is complete, the mixture is held at 50° for 30 minutes and then poured onto ice (400 g) and extracted with diethylether (3 × 80 ml). The ether solutions are combined and an equal volume of 1,4-dioxan added followed by water (25 ml). The resultant mixture is left overnight (16 hrs) at room temperature (20°C). The product is then extracted into dilute hydrochloric acid (3 washings), the acid solution backwashed with ether to remove any dioxan and the aqueous solution poured into excess saturated aqueous potassium carbonate. The product is then extracted into ether, the ether solution dried over magnesium sulphate, filtered and evaporated to yield the ethyl ester of 4-dimethylaminopropyl-4-cyano-4-(m-methoxyphenyl)-3,3-dimethylbutanoic acid (80% yield).

The ester prepared as above (28.8 g) is dissolved in 2.5 N hydrochloric acid (100 ml) and the solution refluxed for 3½ hours and then allowed to cool. The crystals thus formed (21.0 g) are washed with 5N hydrochloric acid and dried. These crystals soften at 270°C and melt at 290°C and their analysis corresponds to $C_{19}H_{29}ClN_2O_3$. The crystals are dissolved in water and the resultant solution neutralised with ammonium hydroxide and then extracted with chloroform (three times). The chloroform solutions are combined, the solvent removed by heating and the residue recrystallised from aqueous methanol to yield 3-(m-methoxyphenyl)-3-($\gamma$-N,N-dimethylaminopropyl)-4,4-dimethyl-2,6-dioxo-piperidine m.pt. 168°–170° (cf. Example 1).

EXAMPLE 4

The following compounds of the invention are also prepared by methods disclosed in this Specification:

3-phenyl-3-($\beta$-N,N-dimethylaminoethyl)-4-methyl-2,6-dioxopiperidine, m.pt. 176°–7°;

3-phenyl-3-($\beta$-N,N-dimethylaminoethyl)-4,4-dimethyl-2,6-dioxopiperidine, m.pt. 192°–4°;

3-phenyl-3-($\beta$-N,N-dimethylaminoethyl)-4,5-dimethyl-2,6-dioxopiperidine, m.pt. 165°–8°;

3-phenyl-3-($\beta$-N,N-dimethylaminoethyl)-5-methyl-2,6-dioxopiperidine, m.pt. 190°–2°;

3-phenyl-3-($\gamma$-N,N-dimethylaminopropyl)-4,4-dimethyl-2,6-dioxo-piperidine, m.pt. 218°–20°;

3-(m-methoxyphenyl)-3-($\beta$-N,N-dimethylaminoethyl)-4-methyl-2,6-dioxo-piperidine, m.pt. 190°–2°;

3-(m-methoxyphenyl)-3-($\beta$-N,N-dimethylaminoethyl)-4,4-dimethyl-2,6-dioxo-piperidine, m.pt. 205°–6°;

3-(m-methoxyphenyl)-3-($\beta$-N,N-dimethylaminoethyl)-4,5-dimethyl-2,6-dioxo-piperidine, m.pt. 165°–70° (isomeric mixture); 172.5°–174° (isomer 1); 198.5°–200° (isomer 2);

3-(m-methoxyphenyl)-3-($\beta$-N,N-dimethylaminoethyl)-5-methyl-2,6-dioxo-piperidine, m.pt. 145°–6°;

3-(p-chlorophenyl)-3-($\gamma$-N,N-dimethylaminopropyl)-4,4-dimethyl-2,6-dioxo-piperidine, m.pt. 213°–5°;

3-(m-methoxyphenyl)-3-($\beta$-N,N-dimethylaminoethyl)-4-methyl-5-ethoxycarbonyl-2,6-dioxo-tetrahydropyridine, m.pt. 143°–4°;

3-(m,p-Dimethoxyphenyl)-3-($\gamma$-N,-methyl,N-(m,p-dimethoxyphenethyl)-aminopropyl)-4,4-dimethyl-2,6-dioxo-piperidine;

3(m,p-Dimethoxyphenyl)-3-($\gamma$-N,N-methyl,N-(m,p- dimethoxyphenethyl)-aminopropyl)-4,5-dimethyl-2,6-dioxo-piperidine;

3-(m,p-Dimethoxyphenyl)-3-(γ-N-methyl,N-2'-(m,p-dimethoxyphenyl)-1'-methyl-ethyl)-aminopropyl)-4,4-dimethyl-2,6-dioxo-piperidine;

3-(m,p-Dimethoxyphenyl)-3-(γ-N-methyl,N-(2'-(m,p-dimethoxyphenyl)-1'-methyl-ethyl)-aminopropyl)-4,5-dimethyl-2,6-dioxo-piperidine.

3-Phenyl-3-(β-N-benzyl-N-methyl-aminoethyl)-4,4-dimethyl-2,6-dioxo-piperidine, m.pt. 167°–8°;

3-Phenyl-3-(β-N-methylaminoethyl)-4,4-dimethyl-2,6-dioxo-piperidine hydrochloride hemiethanolate m.pt. 233°–5°;

3-(m-Methoxyphenyl)-3-(β-N,N-dimethylaminoethyl)-4-ethyl-2,6-dioxo-tetrahydropyridine, m.pt. 166°; and 3-(m-Methoxyphenyl)-3-(β-N,N-dimethylaminoethyl)-4-methyl-5-ethoxycarbonyl-2,6-dioxo-piperidine m.pt. 123°.

The following compounds are novel intermediates obtained during the preparation of the pharmacologically active compounds of the invention:

4-(β-N,N-dimethylaminoethyl)-4-cyano-4-phenyl-3-methyl-butanoic acid ethyl ester;

4-(β-N,N-dimethylaminoethyl)-4-cyano-4-phenyl-2-methyl-butanoic acid ethyl ester;

4-(β-N,N-dimethylaminoethyl)-4-cyano-4-(m-methoxyphenyl)-2-methyl-butanoic acid ethyl ester;

4-(β-N,N-dimethylaminoethyl)-4-cyano-4-(m-methoxyphenyl)-3-methyl-butanoic acid ethyl ester;

4-(β-N,N-dimethylaminoethyl)-4-cyano-4-phenyl-3,3-dimethylbutanoic acid ethyl ester;

4-(β-N,N-dimethylaminoethyl)-4-cyano-4-(m-methoxyphenyl)-3,3-dimethyl-butanoic acid ethyl ester;

4-(β-N,N-dimethylaminoethyl)-4-cyano-4-(m-methoxyphenyl)-2,3-dimethyl-butanoic acid morpholine amide;

4-(β-N,N-dimethylaminoethyl)-4-cyano-4-(m-methoxyphenyl)-2,3-dimethyl-butanoic acid morpholine amide oxalate.

4-(β-N,N-dimethylaminoethyl)-4-cyano-4-phenyl-2,3-dimethyl-butanoic acid morpholine amide.

4-(γ-N,N-dimethylaminopropyl)-4-cyano-4-phenyl-3,3-dimethyl-butanoic acid ethyl ester;

4-(γ-N,N-dimethylaminopropyl)-4-cyano-4-(p-chlorophenyl)-3,3-dimethyl-butanoic acid ethyl ester;

4-(γ-N,N-dimethylaminopropyl)-4-cyano-4-(m-methoxyphenyl)-3,3-dimethyl-butanoic acid ethyl ester;

4-(β-N-benzyl-N-methylaminoethyl)-4-cyano-4-phenyl-3,3-dimethyl-butanoic acid ethyl ester;

4-(β-N-benzyl-N-methylaminoethyl)-4-cyano-4-(m-methoxyphenyl)-3,3-dimethyl-butanoic acid ethyl ester;

4-(γ-N,N-dimethylaminopropyl)-4-cyano-4-(m-methoxyphenyl)-2,3-dimethyl-butanoic acid ethyl ester;

4-(β-N-methyl-N-(m,p dimethoxyphenethyl)-aminoethyl)-4-cyano-4-(m,p dimethoxyphenyl)-3,3-dimethyl-butanoic acid ethyl ester; and 4-(β-N-methyl-N-(m,p-dimethoxyphenethyl)-aminoethyl)-4-cyano-4-(3',5'-dimethoxyphenyl)-3,3-dimethyl-butanoic acid ethyl ester.

What we claim is:
1. Compounds having the formula

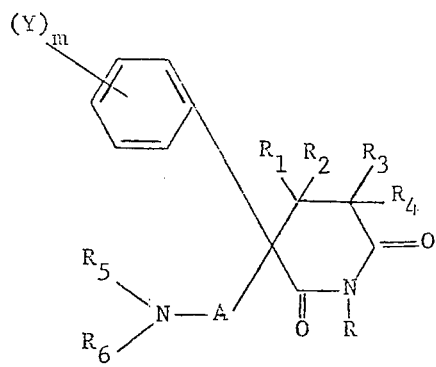

wherein
R represents hydrogen or $C_1$–$C_4$ alkyl, $R_1$, $R_2$ and $R_3$ independently represent hydrogen or $C_1$–$C_4$ alkyl, $R_4$ represents hydrogen, or $C_1$–$C_4$ alkyl, provided that at least one of $R_1$, $R_2$, $R_3$, and $R_4$ represents alkyl, or $R_1$ together with $R_3$ represents a second valency bond joining their immediately adjacent ring carbon atoms, and $R_2$ and $R_4$ independently represent hydrogen or $C_1$–$C_4$ alkyl;
Y represents $C_1$–$C_4$ alkyl optionally substituted by hydroxy, or $C_1$–$C_4$ alkoxy, halogen or trifluoromethyl;
m represents zero or an integer up to 5;
A represents $C_1$–$C_6$ alkylene;
$R_5$ represents $C_1$–$C_4$ alkyl, optionally substituted by $C_3$–$C_6$ cycloalkyl, or $C_3$–$C_6$ cycloalkyl and $R_6$ represents hydrogen or $C_1$–$C_4$ alkyl or $R_5$ together with $R_6$ represents an alkylene radical optionally interupted by oxygen or nitrogen and which together with the amino nitrogen atom constitute a saturated five or six membered heterocyclic ring, and pharmaceutically acceptable acid addition salts and quaternary amine salts thereof.

2. The compound of claim 1 which is 3-(m-methoxyphenyl)-3-(γ-N,N-dimethylamino-dimethylaminopropyl)-4,4-dimethyl-dioxo-piperdine.

3. Compounds of the formula:

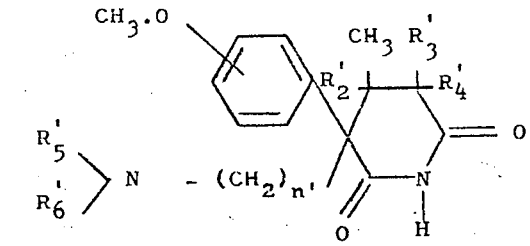

wherein
n' represents 2 or 3;
$R_2'$, $R_3'$, and $R_4'$ independently represent hydrogen or methyl, and
$R_5'$ and $R_6'$ independently represent methyl or ehtyl, and pharmaceutically acceptable acid addition salts thereof.

* * * * *